United States Patent [19]
Zelechonok

[11] Patent Number: 5,920,006
[45] Date of Patent: Jul. 6, 1999

[54] LIQUID CHROMATOGRAPHIC PUMP AND VALVE ASSEMBLY

[75] Inventor: Yury Zelechonok, Northbrook, Ill.

[73] Assignee: Digichrom, Inc., Northbrook, Ill.

[21] Appl. No.: 08/876,568

[22] Filed: Jun. 16, 1997

[51] Int. Cl.⁶ .......................... G01N 30/18; G01N 30/20; G01N 30/22
[52] U.S. Cl. ......................................... 73/61.56; 73/61.55
[58] Field of Search ................................. 73/61.55, 61.56

[56] References Cited

U.S. PATENT DOCUMENTS

| | | | |
|---|---|---|---|
| 3,847,507 | 11/1974 | Sakiyama et al. | 417/22 |
| 3,922,115 | 11/1975 | Coe et al. | 417/374 |
| 4,102,782 | 7/1978 | Saito et al. | 73/61.55 X |
| 4,233,156 | 11/1980 | Tsukada et al. | 73/61.56 X |
| 4,311,856 | 1/1982 | Boldvin et al. | 73/61.56 X |
| 4,406,158 | 9/1983 | Allington | 73/61.57 |
| 4,883,409 | 11/1989 | Strohmeier | 417/43 |
| 4,939,943 | 7/1990 | Struhmeier | 73/864.21 |
| 4,980,296 | 12/1990 | Trisciani et al. | 73/61.52 X |
| 5,637,208 | 6/1997 | Dourdeuille | 210/90 |
| 5,846,832 | 12/1998 | Oetner et al. | 422/50 X |

*Primary Examiner*—Thomas P. Noland
*Attorney, Agent, or Firm*—Charles F. Lind

[57] ABSTRACT

The disclosed HPLC syringe or pump has valve components housed immediately adjacent a defined pump chamber, effectively minimizing dead flow passage spaces and the needed volume of flushing liquid between tests. The mated surfaces of the valve components are biased together with forces substantially proportional to the pumped liquid pressures, and the drive for moving the syringe chamber piston also and concurrently shifts the valving components before driving the piston in the pump chamber, effectively minimizing leakage while allowing valve shifting without excessive wear. The chamber piston drive is comprised of concentrically positioned lead screw and pump cylinder structure keyed to the valve components. Spaced seals isolate the defined pump chamber from the piston drive lead screw for minimizing damaging solvent contact with the screw, and passages allow for flushing the pump chamber walls between the seals of solvent left thereon to minimize solvent crust buildup thereon.

17 Claims, 6 Drawing Sheets

SOLVENT DELIVERY

PUMP REFILL

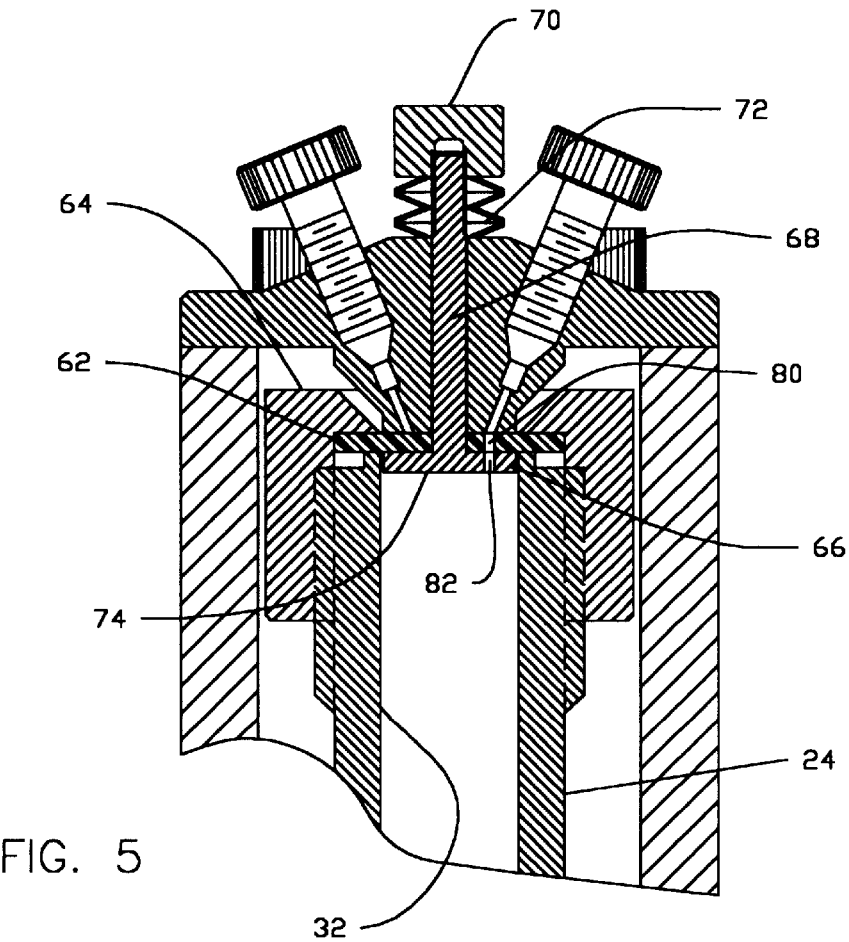
FIG. 5
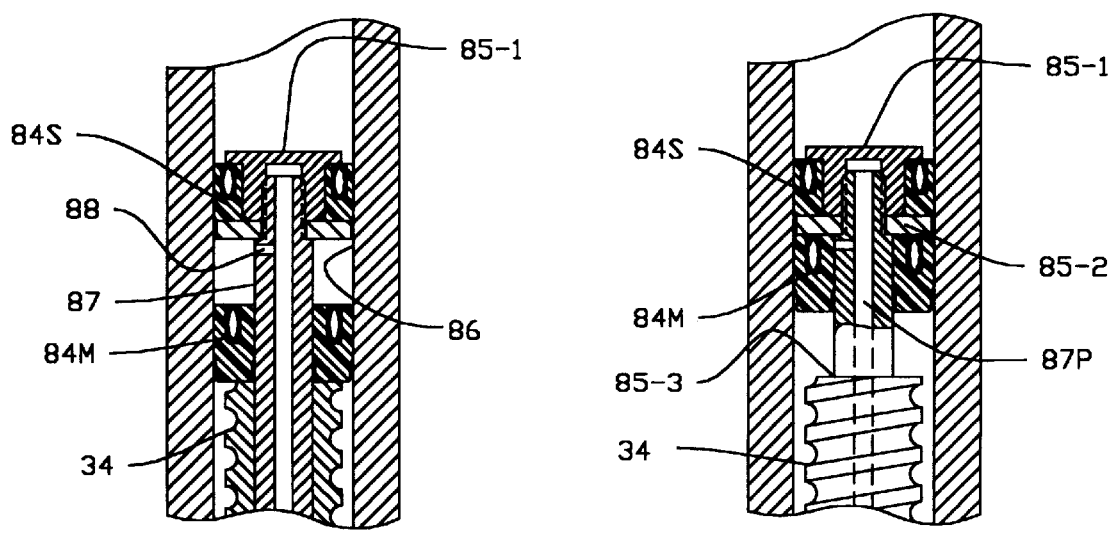
FIG. 8A
FIG. 8B

FIG. 7A  SOLVENT DELIVERY

FIG. 7B  PUMP REFILL

LIQUID CHROMATOGRAPHIC PUMP AND VALVE ASSEMBLY

FIELD OF THE INVENTION

This invention relates to liquid pump and valve mechanisms (commonly known as syringe pumps) for use in liquid chromatographic systems for analytical chemical studies, the mechanisms directing small precise quantities of sample and solvent liquids to and through a column for isolating different sub phases of the sample.

BACKGROUND OF THE INVENTION

Liquid chromatography (hereinafter sometimes referred to with the abbreviation LC) relates to the spatial separation of different sub phases (compounds or components) of a sample due to the different affinity of these sub phases with an absorbent. A typical LC system might comprise a separation column filled with the absorbent (as very fine power for example), a mechanism for discharging a liquid sample, a pump for forcing one or more liquid solvents and the liquid sample to and through the column, and a detector sensitive to different physical characteristics of the sub phases to sense them passing through the column. The overall concept relates to the fact that due to different respective affinity rates (absorption and desorbtion) of the different sample sub phases with the absorbent, these sub phases will penetrate through the column at different rates. The solvent is pumped to generally high pressures to pass at an accurate and substantially steady flow rate through the sample and into the column, whereby the sub phases might become isolated and axially spaced out as narrow bands passing through the column with the solvent, to be sensed by the detector. The different sub phases might then be identified as well as each's possible percentage within the sample determined. Generally, only a small quantity of liquid sample is used (a few mcls), and the volume of the column is likewise small (perhaps only a few mls).

A most critical aspect of LC systems is providing for accurately controlled pumping of the solvent, at the needed high pressures (several thousand psi) and at specific quite low flow rates. Two basic pump concepts are common: the reciprocating plunger-cylinder type and the piston-cylinder or syringe type. This invention is related to the piston-cylinder or syringe type pump.

A prior art piston-cylinder or syringe type pump might have a piston movable in cylinder structure for defining an expansible pump chamber, with a seal on the piston sliding along the inside surface of the cylinder wall. The piston might be powered by a ball-screw linear drive mechanism. Such linear drives rotatably support a member interconnected with a lead screw by many balls, and a motor drives the rotatable member to axially shift the screw relative to the rotating member; and there is a drive connection linking this axial screw movement to the piston. However, if the pumped solvent should leak past the piston seal and contact certain components of the linear drive, the drive can be damaged and/or its efficiency reduced; meaning that special pump designs have been used to prevent such from happening.

One LC pump design has had the drive screw concentrically aligned with the cylinder, but the linear drive components are located well beyond the bottom of the cylinder and separated therefrom by a sealing arrangement, effective for precluding solvent leakage from the defined pump chamber from ever reaching the drive components. An alternative design approach has spaced the drive screw laterally off-set from but parallel to the cylinder, and has had a rod connected to the piston and fitted concentrically within the cylinder and also connected to the adjacent parallel screw. Thus, solvent leakage from the pump chamber can drain harmless along the rod without contacting the linear drive components. However, both drive designs add appreciably to the overall size and cost of the solvent pump.

In such LC pumps, valving and sample injection port structures are commonly provided in closed liquid conveying passages between the sample and solvent reservoirs, the pump chamber and the column. This includes inlet and outlet valving for solvent flow control relative to the pump chamber, which frequently might be check valves that are pressure activated, meaning that such are less responsive and reliable than independently powered valves. Check valves further create significant dead space of added volume in the closed flow system. Positive valving might improve on these drawbacks, but such would generally require power shifting means and appropriate operating and timing controls, adding to both cost and complexity. The sample injection port might be provided as part of the valving, into the solvent conveying passage between the pump chamber and the column, and such frequently might be spaced from each by long flow passages, which tend to create additional dead spaces within the closed system. As the flow passages have to be flushed whenever a different solvent is to be used in any subsequent tests made with the same equipment, dead spaces will add to the solvent volume needed for effective flushing. Moreover, high seating pressures between the stationary and movable members of the valving are needed to preclude leakage of the contained high liquid pressures, and many valving arrangements use springs for generating forces needed for obtaining these seating pressures. However, as spring forces might be continuous, the high seating pressures are excessive for precluding leakage at lower than maximum pumping pressures, meaning that premature wear of the seated valve components might occur when the valve members are shifted at lower pressures.

Thus, commercial pump and valve devices (or syringe pumps) have been both large and costly, compared to or in spite of only relatively small volumes of liquid sample and solvents being handled. Both check valves and positive valving with the needed secondary power shifting means and its control have operational drawbacks, add to the size, cost and complexity of the designs; while yet such designs are the most common apparatus commercially available. The separation of the pump and valving has contributed to the added size, awkwardness of set-up, and costs, and reduced reliability of operation. Prior pump designs with the abundant dead space occupied by solvent adds both extensive flushing time and solvent volumes needed between test runs of different solvents.

SUMMARY OF THE INVENTION

Basic objects of this invention are to provide a syringe or LC pump and valve assembly that can be economically manufactured, that will be compact and essentially unitary for space efficiency and ease of movement and set-up, that will be reliable, accurate and versatile in use, that will have an expected extended service life with minimal solvent leakage or potential damaging of the linear pump drive, that can pump sufficient volumes of solvent at needed pressures and flow rates during an LC test, and that has minimal dead space volume for economical solvent flushing between tests of different solvents.

Important features of this invention include providing an LC pump and valve assembly that has valve components in close proximity with pump components and immediately adjacent a defined pump chamber thereof, so that both the pump and valve components can be housed by common frame structure; and further of providing that mated seating surfaces between stationary and movable valve members are biased together with forces proportional to the pumped liquid pressures, so that the valve can be operated essentially without leakage and yet can be shifted without excessive surface wear between operative positions with the pumped liquid pressures being less than maximum.

Yet other features of this invention provide an LC pump and valve assembly that has sample and solvent flow directing valving that is power shifted mechanically by the pump drive, and automatically upon the initial operation of the pump drive, such as by having a pump cylinder housing mounted to rotate about its longitudinal center axis and one valving component keyed to the cylinder housing to be shifted therewith, and having linkage between the reversible motor driving the pump drive also then being operable to power rotate the pump cylinder housing and valving component for shifting as needed.

Further important features of this invention provide an LC pump and valve assembly with structures that allow a piston-cylinder pump structure to be powered by a linear drive lead screw concentrically positioned in the pump cylinder and closely adjacent the defined pump cylinder while yet precluding solvent leakage past the piston from reaching the linear drive, for minimizing the potential of damaging the drive, and also that allow the inside wall of the cylinder cooperating with the piston to be cleansed of solvent left thereon after the pumping cycle for minimizing any solvent film or crust buildup thereon that might reduce the overall pump efficiency.

BRIEF DESCRIPTION OF THE DRAWINGS

These and other objects, features or advantages of the invention will be more fully understood and appreciated after consideration of the following description of the invention, which includes as a part thereof the accompanying drawings, wherein:

FIG. 5 is an enlarged sectional view of part of the assembly of FIG. 2, showing greater clarity of detail;

FIGS. 7A, 7B and 7C are part of the valving control used to connect the sample, column and solvent, and optional solvent port, FIGS. 7A and 7B showing the valve respectively in the solvent delivery and solvent refill operating positions and FIG. 7C showing a component detail as seen generally from line 7C—7C in FIG. 7A;

FIGS. 8A and 8B are sectional views of the piston in FIG. 2, except showing its components respectively in the solvent delivery and solvent refill operating positions;

DETAILED DESCRIPTION OF PREFERRED EMBODIMENTS OF THE INVENTION

Figure 1:
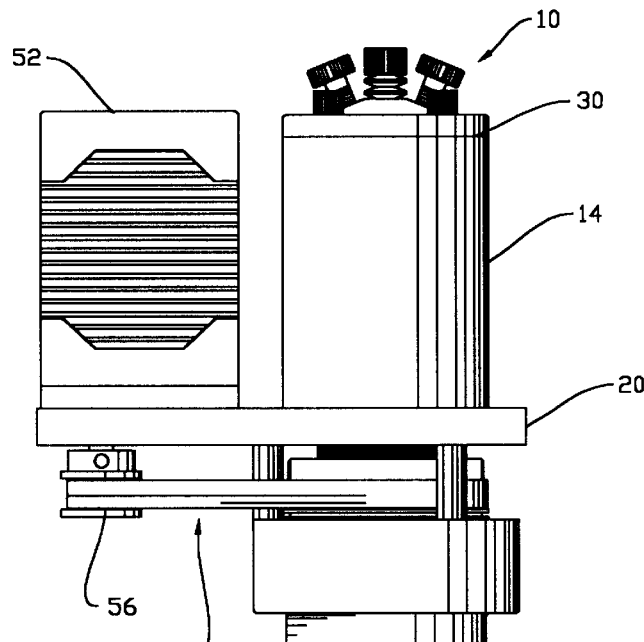
FIG. 1 is a side elevational view of a first embodiment of pump and valve assembly formed according to the invention, shown in a solvent delivery or run operating position.
Figure 2:
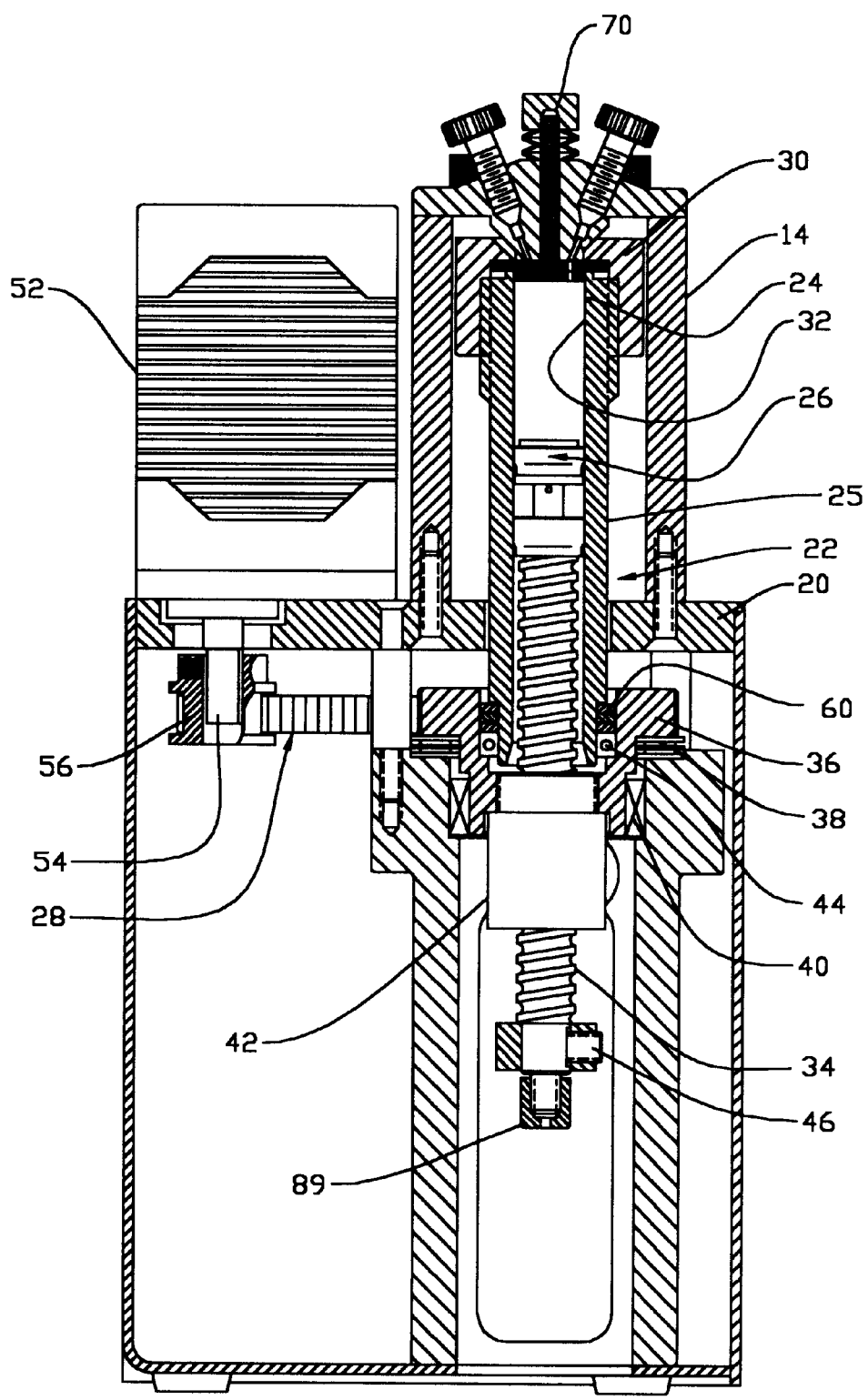
FIG. 2 is a generally centered sectional view of the assembly shown in FIG. 1.

The invention is herein embodied with a liquid chromatographic system 10 (FIGS. 1, 2 and 6) that utilizes a column 12 through which sample and solvent liquids are passed, the invention being comprised as an improved pump and valve assembly 14 for directing the sample and solvent liquids from containment in respective reservoirs (sample syringe 16 and solvent bottle 18) to the column 12, where the output could be sensed by means of conventional detector instrument 19.

The pump and valve assembly 14 is illustrated as including frame structure 20; a pump 22 with a cylinder 24 and cooperating piston 26 therein, and reversible drive means 28 to move the piston 26 within the cylinder to provide respective solvent filling and pumping cycles from the pump 22; and valving 30 connected between the column 12, sample and solvent reservoirs 16 and 18, and pump 22 for directing flow of the liquids as needed, with the frame structure 20 effectively supporting the pump and valve components in close proximity and substantially as a unitary assembly.

Pump cylinder 24 is comprised as tubular housing 25 open at both ends, but the pump chamber end is closed by structure including the valving 30. The piston 26 cooperates in sealed relationship with the pump cylinder 24, so that a variable volume pump chamber 32 is defined at the closed cylinder end adjacent the valving 30 as the piston is axially shifted in the cylinder. The reversible drive means 28 is illustrated as including a lead screw 34 connected to the piston 26, a drive member 36 rotatably supported by bearings (axial thrust bearing 38 and radial bearing 40) by the frame structure 20 adjacent the open pump cylinder end, and a conventional ball nut mechanism 42 between the drive member 36 and lead screw 34.

The housing 25 of the pump cylinder 24 can be rotated about its longitudinal center axis relative to the frame structure 20, supported at lower end by bearings 44 radially of drive member 36 and at upper end by structure of the valving 30. However, the cylinder housing is limited to approximately 60 degrees of rotation, by a cross pin 46 (FIGS. 1, 2, 4A and 4B) keyed to the screw 34 with its ends contained between spaced axially extended guides 48 and 49 on the frame structure 20, rollers 50 on the pin ends minimizing drag upon any axial screw movement.

A reversible electric gearmotor 52 mounted on the frame structure 20 has its output shaft 54 keyed to pulley 56, and a drive belt 58 is trained over the pulley 56 and a pulley 57 secured to or contoured integrally with the drive member 36, operable to power rotate the drive member 36. Friction discs 60 can be provided between the cylinder housing 25 and drive member 36, to create a mechanical linkage between them, so that rotation of the drive member can also cause rotation of the cylinder housing in the same direction. Even though the piston 26 and screw 34, and the piston and pump cylinder 24 might fit together or cooperate quite snugly, these components can be rotated relative to one another, so that the drive member 36 can be rotated to drive and axially shift the screw 34 and pump piston 26 relative to the cylinder 24 even after the cylinder housing 25 can no longer be rotated, as when the cross pin rollers 50 have been butted against either guide 48 or 49.

The structure of the valving 30 (FIGS. 5, 6, 7A and 7B) includes a disc 62 having its periphery trapped between the end of cylinder housing 25 and annular flange region of a cap 64 threaded onto the cylinder housing exterior. The valve disc 62 has opposed annular faces 62F and 62P, where valve face 62F cooperates against a seat formed on the frame structure 20 and the other valve face 62P cooperates against a seat on a separate plunger 66. A plunger stem 68 is fitted through a bore in the frame structure 20 to a connection with exterior knob 70; and resilient compression spring 72 around the stem between the knob 70 and frame structure 20 biases the frame and plunger seats against the valve disc faces. The plunger 66 has opposed its valve disc seat a face 74 having an area about the same size as or possibly even larger than the valve disc seat, the plunger face 74 being directly exposed to pressures in the pump chamber 32. The longitudinal axes of the cylinder 24, cylinder housing 25, screw 34, valve disc 62, plunger 66 and plunger stem 68 might all coincide. The cylinder housing 25, valve disc 62 and plunger 66 are connected to move or rotate together as a unit.

Figure 7C:
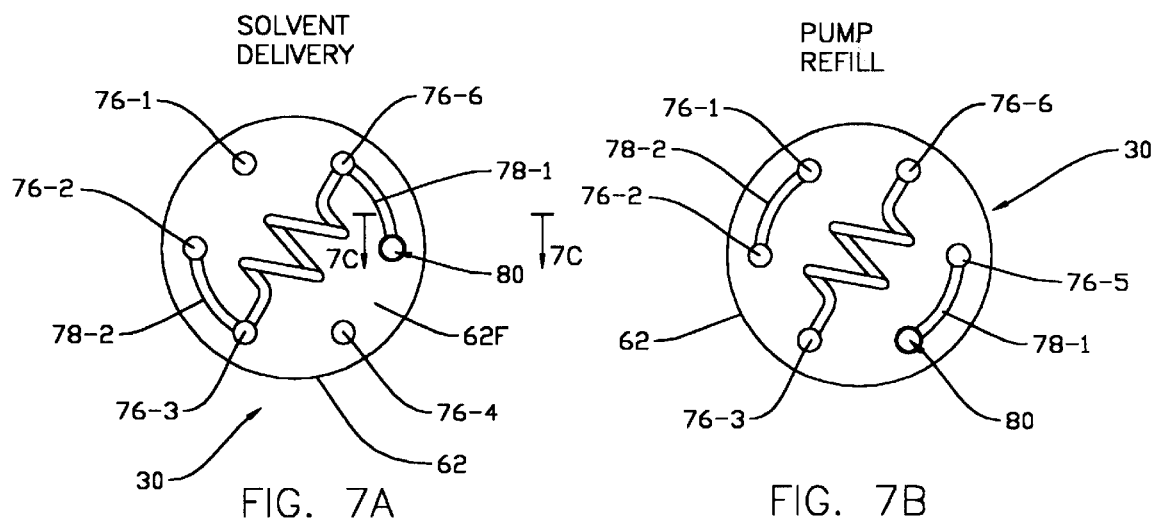
Figure 6:
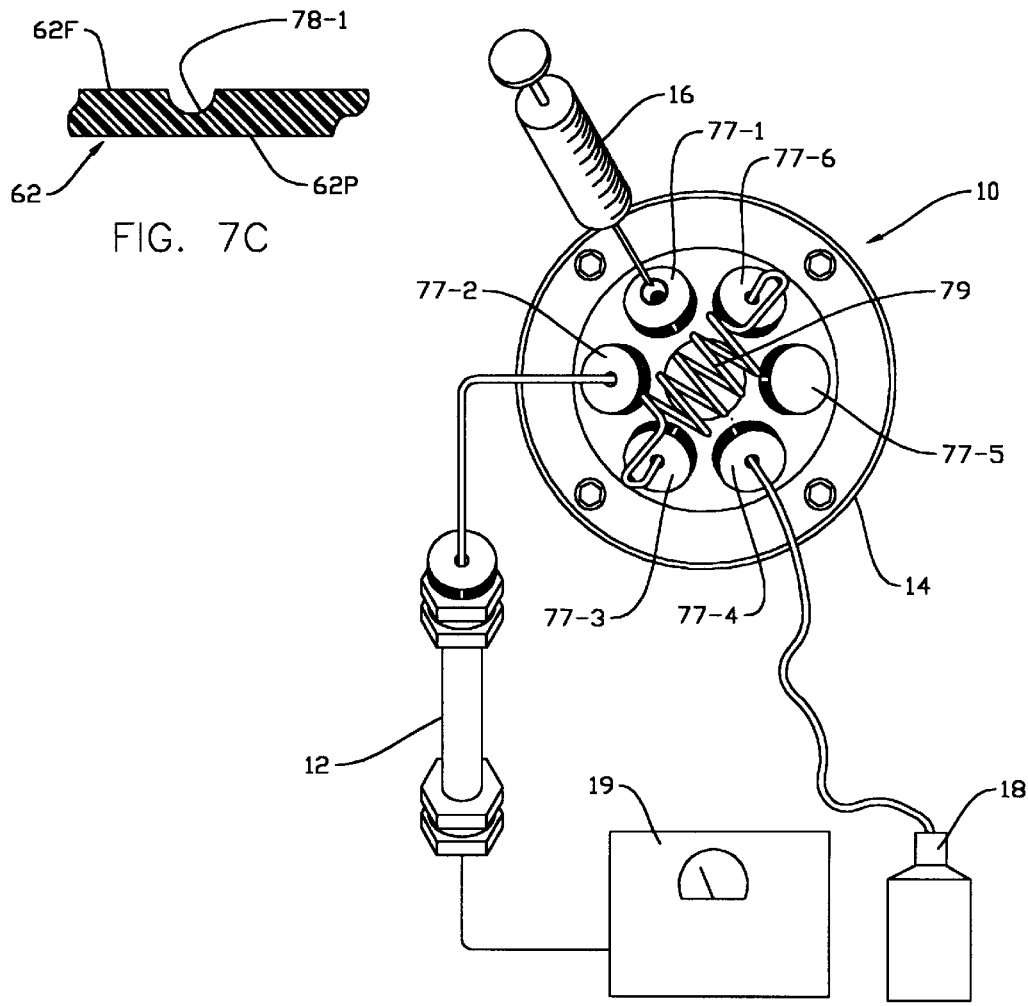
FIG. 6 is a top plan view of the pump and valving of the previous figures, showing also operational connections of the sample syringe, liquid chromatography column, solvent reservoir, exterior loop and optional port.

The frame structure seat has six ports (their locations being illustrated in phantom and identified as 76-1, 76-2, 76-3, 76-4, 76-5 and 76-6 in FIGS. 7A and 7B) equally spaced circumferentially (at 60 degree spacings) around and equally spaced radially from the longitudinal axes of the cylinder 24, etc., the ports communicating via threaded bores in the frame structure to conventional fittings secured therein. As illustrated in FIG. 6, the liquid sample reservoir 16 communicates with the port 76-1 via conventional syringe fitting 77-1, and the column 12 and solvent reservoir 18 respectively communicates with the ports 76-2 and 76-4 via appropriate fittings 77-2 and 77-4. Further, the two opposite ports 76-3 and 76-6 (at approximately 180 degree spacings) are connected together by exterior tubing 79 via appropriate fittings 77-3 and 77-6, and port 76-5 communicates with fitting 77-5 which as illustrated is capped closed.

On the valve disc 62, the annular face 62F that cooperates against the frame structure seat has two opposite channels 78-1 and 78-2 each extended over approximately a 60 degree arc, the channels being located opposite one another to have approximately 120 degree spacings therebetween. A bore 80 extends through the valve disc between its opposite faces, and is aligned with a bore 82 through the plunger 66.

Figure 4A:
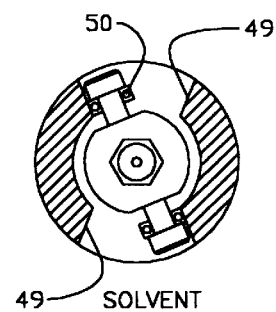
FIGS. 4A and 4B are sectional views as seen generally from line 4—4 in FIG. 1, except showing the components respectively in the solvent delivery and pump refill operating positions.
Figure 4B:
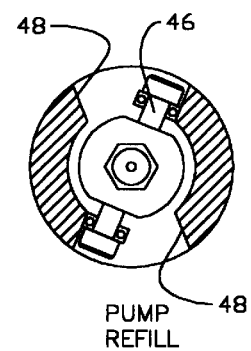
Figure 3:
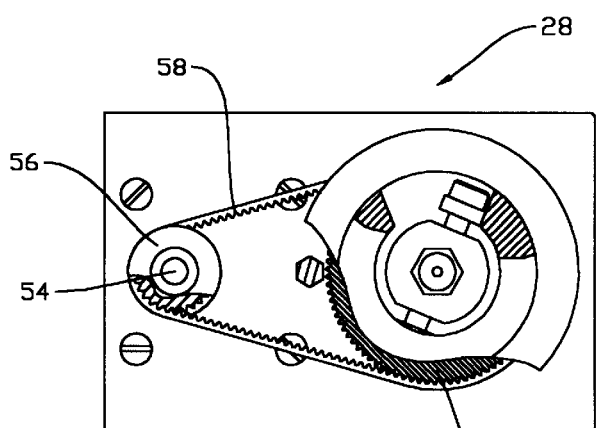
FIG. 3 is a bottom view, partly in section for clarity of disclosure, of the assembly of FIG. 1, except showing it in a solvent refill operating position.

The two operative positions of the valve disc 62 are illustrated in FIGS. 7A and 7B, incidental with the cylinder housing being rotated between the two positions illustrated in FIGS. 4A and 4B. FIG. 7B corresponds to the filling cycle where sample reservoir 16 and column 12 communicate via ports 76-1 and 76-2 and channel 78-2, and where the solvent reservoir 18 (port 76-4) communicates with pump chamber 32 via aligned ports 80 and 82 (channel 78-1 leading only to the capped port 76-5). FIG. 7A corresponds to the pumping or solvent delivery cycle where the sample and solvent reservoirs 16 and 18 are isolated (the corresponding ports 76-1 and 76-4 being closed against valve disc face 62F), and where the pump chamber 32 (via aligned ports 80 and 82) now at the port 76-5 communicates with the column 12 (port 76-2) via channel 78-1, exterior tube 79 and channel 78-2.

Alternatively, if another pump and valve assembly (not shown) were being used for another solvent liquid contained in a separate solvent bottle (not shown), the outlet from the column port (corresponding to port 76-2) of the other pump and valve assembly could be directed via tubing (not shown) through the illustrated valving, via the fitting 77-5 and its associated port 76-5, so that with the valve disc in the pumping or solvent delivery position of FIG. 7A, solvent would flow between the ports 76-5 and 76-2 via the valve disc channels 78-1 and 78-2 and exterior tubing 79. This mode of operation probably will occur only with concurrent operation of the pump assembly 14 at its proposed rate of discharged, although the secondary solvent routing would be the same without the operation of the pump assembly 14.

The pump and valve assembly 14 as thus far described provides that rotation of the drive member 36, via the reversible drive means 28 including the gearmotor power drive 52, will shift the lead screw 34 and connected piston 26 axially within the cylinder 24; effectively during the filling cycle to shift the piston 26 to increase the volume of pump chamber 32, and during the solvent pumping cycle (with the drive member being oppositely rotated) to shift the piston to decrease the chamber volume. The drive member rotation at the beginning of both the filling and pumping cycles, via the link or bias provided by the friction discs 60, also rotates the cylinder housing 25, which shifts the valving 30 and specifically the valve disc 62 and plunger 66, to a corresponding filling or pumping cycle positions (either FIG. 7B or 7A respectively). With the seating pressures being proportional to the pumped liquid pressures (not bases on fixed forces from springs or the like), and with the axial reversal of the piston in the cylinder at the beginning of the refilling cycles whereupon the volume of the pump chamber 32 expands to quickly reduce high chamber pressures, the seating pressures between the mated moving and stationary valving components will correspondingly be quickly reduced, making possible the accompanying rotational shift of the valving components to the filling position of FIG. 7B without excessive wear of the valving component seats.

Of interest further, the piston 26 (FIGS. 8A and 8B) in the inventive assembly 14 disclosed herein has axially spaced annular sealing regions 84L and 84M cooperating with the pump cylinder 24, region 84S being immediately adjacent the defined pump chamber 32 and the region 84M being next to sealing region 84S and remote from the pump chamber 32. The sealing regions 84S and 84M can be formed of conventional annular spring seals. Further, seal 84M is fixed axially of the piston between plates 85-1 and 85-2, while seal 84M can axially slide sealinqly along screw stem 87 between plate 85-2 and screw shoulder 85-3, operable to define a variable volume chamber 86 between the sealing regions.

The screw stem 87 can be comprised of a separate tube member fitted in an axial bore through the screw, defining an axial flow passage 87P extended between a port 88 in the stem open to the chamber 86 and a fitting 89 on the opposite screw end, where then a flexible line 89A can be held thereby to communicate with a source of cleaning liquid contained in reservoir 90 located remotely of the assembly 14. The separate stem tube 87 can be of stainless steel or durable plastic material suited to resist chemical attacks from any pumped solvent or cleaning liquid. The screw 34 can thus effectively be isolated from contact with either a corrosive solvent or cleaner liquid, for protecting the screw 32 which typically will be formed from structural steel material.

The sealing regions 84S and 84M of the piston 26 become separated during the pumping cycle (FIG. 8B) suited to have cleaning liquid from the reservoir 90 admitted to the chamber 86 for flushing the inside wall of the cylinder 24, and are moved adjacent one another (FIG. 8A) to have the cleaning liquid discharged from the chamber via the cleaning port 88 during the filling cycle. This piston construction and operation both flushes any pumped solvent from the cylinder wall with the cleaning liquid and it precludes any solvent that might have leaked past the sealing region 84S during the pumping cycle and in the cleaning chamber 86 from passing the sealing region 84M to reach the ball nut drive mechanism 42 and lead screw 34 of the reversible drive means 28. The cleaning liquid might be water, aqueous solutions of different Ph and salt concentrations, alcohol or other mixture effective against the pumped solvent. The operating life of the drive and pump components with this flushing operation should be appreciably extended, while simplifying or reducing other maintenance efforts.

Figure 9:
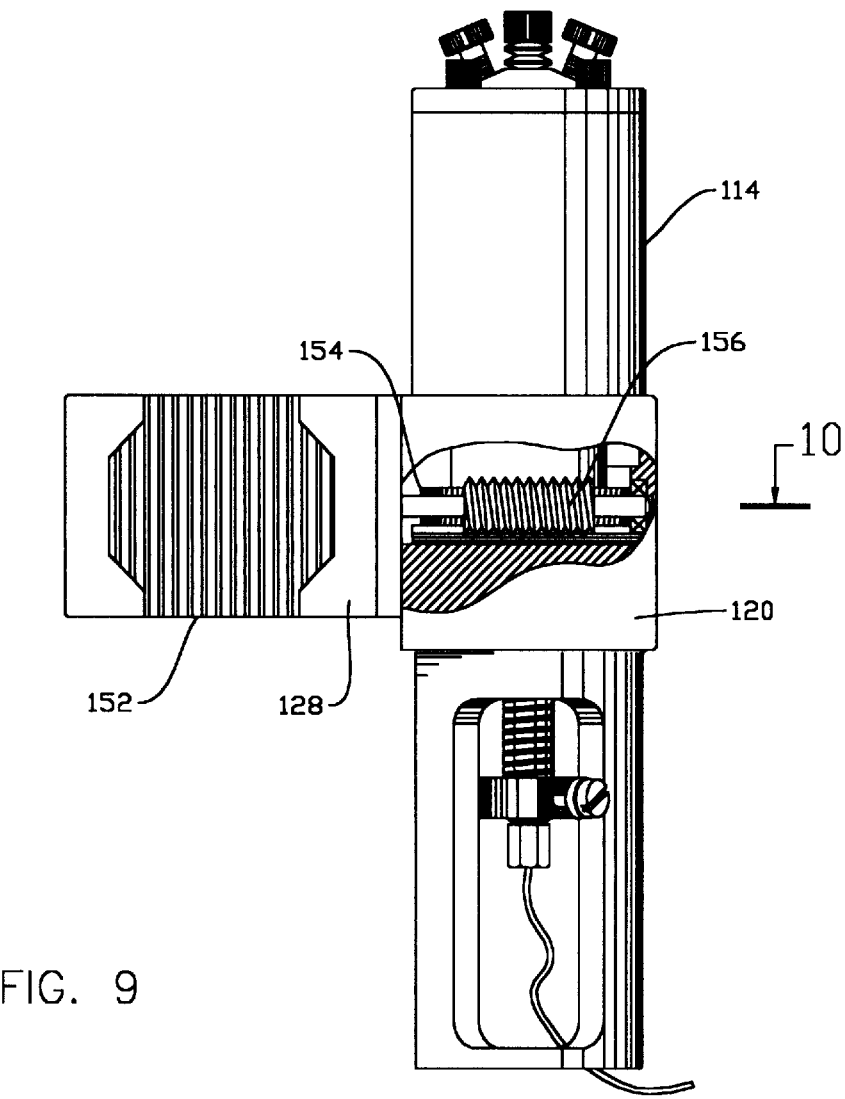
FIG. 9 is a side elevational view, partly in section, of a second embodiment of pump and valve assembly formed according to the invention.
Figure 10:
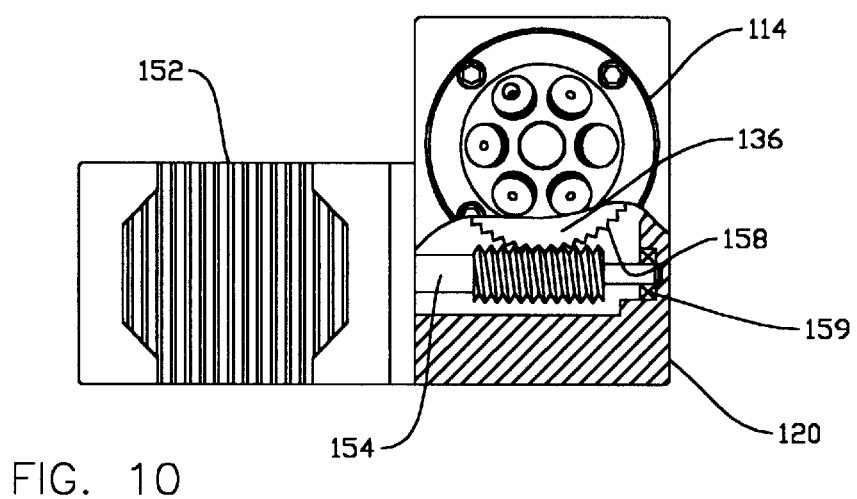
FIG. 10 is a top view of the assembly of FIG. 9, partly in section as seen, from line 10 in FIG. 9.

A first alternate embodiment of a proposed pump and valve assembly 114 is illustrated in FIGS. 9 and 10, with components the same as or related to like components of the assembly 14 being identified with the same number increased by one hundred. A major specific difference between assemblies 14 and 114 is the form of drive means 128 operable to power rotate the drive member 136. Thus, a reversible electric motor 152 replaces the reversible electric gearmotor 52, the motor shaft 154 is extended transverse to the axis of rotation of drive member 136 cooperating with the lead screw 34 via the ball and nut mechanism 42, and a worm 156 keyed to the motor shaft 154 or coupled extension meshes with gearing 158 formed on or secured to the drive member 136. The worm shaft 154 or extension might be supported by bearings 159 held in the frame structure 120. Worm/shaft rotation in either direction will correspondingly rotate the drive member 136 in either direction to axially shift the screw 34 and piston 26 for performing the filling or pumping cycle, and further will rotate the cylinder housing 25 and connected valve disc 62 as needed to operate the pump valving 30. The high translation ratio of the worm drive allows the use of stepper motor 152 (compared to the motor shaft speed being reduced via the unitary gear reduction of the gearmotor 52) to rotate the drive member 136 with the needed torque and speed of rotation, for axially shifting the drive screw 34 and piston 26 for pump operation. This embodiment might offer reduced costs and size, not needing an expensive gearmotor or larger frame structure for holding the gearmotor 52 spaced adjacent the pump cylinder with its output shaft 54 extended parallel to the common cylinder and screw axis.

Figure 11:
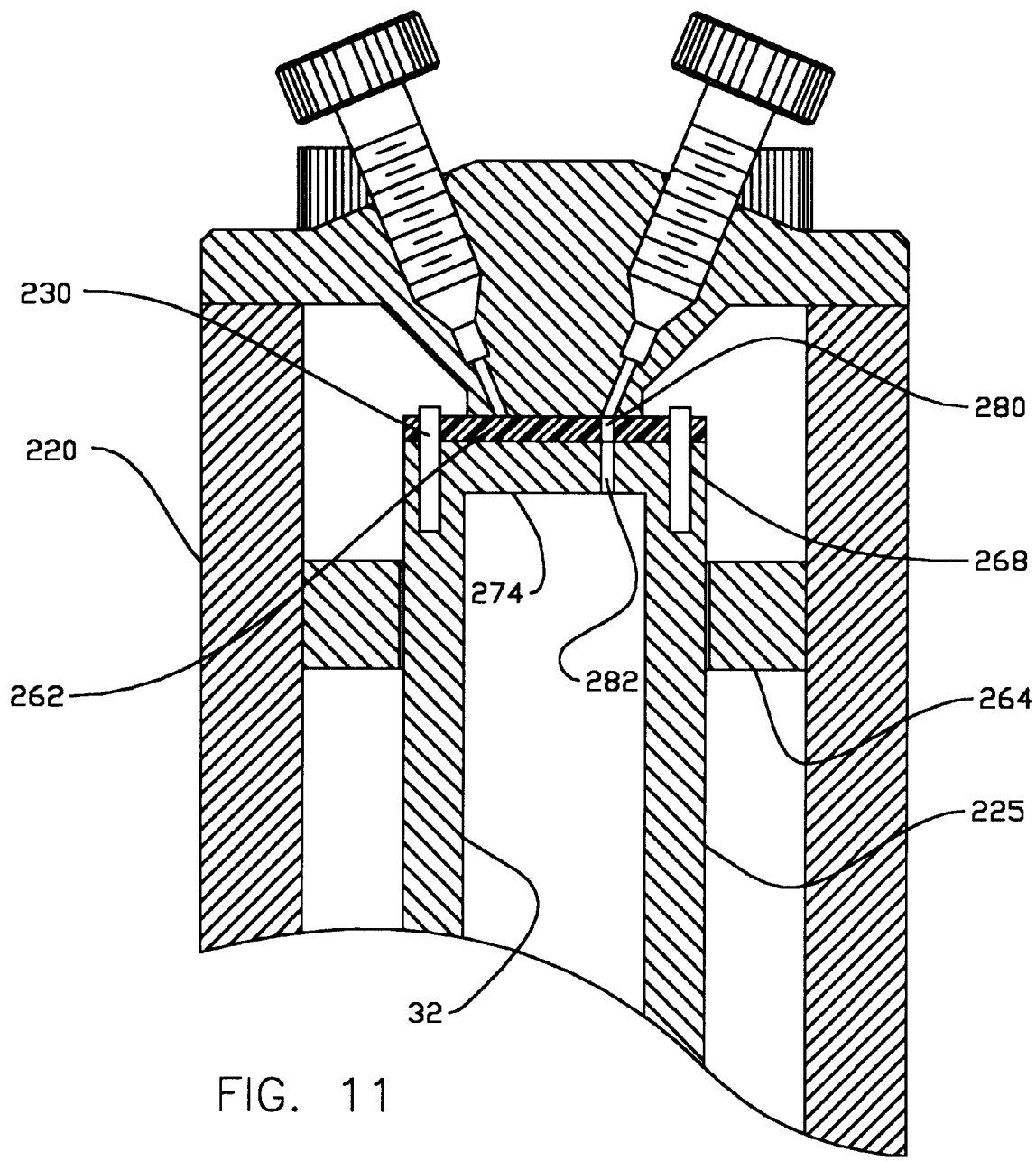
FIG. 11 is a sectional view similar to FIG. 5, except of a third embodiment of pump and valve assembly formed according to the invention.

A second alternate embodiment of a pump and valve assembly 214 is illustrated in FIG. 11, again with the same or related like components of the assembly 14 being identified with the same number increased by two hundred. In this embodiment, the cylinder housing 225 has a cross wall 274 closing the pump chamber 32 and valving end thereof. The valving 230 includes disc 262 secured to the cylinder wall 274, as by peripheral pins 268. Annular member 264 positioned between the outside of the cylinder housing 225 and the frame structure 220 supports the valve end of the cylinder housing, to allow it to be rotated in two direction through its limited 60 degrees arc. The valve disc 262 has valve face 62F that cooperates against a seat formed on the frame structure 220 where the other valve face 62P cooperates against the cylinder cross wall 274, with aligned throughbores 280 in the valve disc and 282 in the cross wall. The effective area of the pump chamber 32 will be generally as large as or larger than the valve disc face 262F seated against the frame structure 220. The frame seat and valve disc face 62F will be biased together by seating pressures proportional to the pumped liquid pressures in the chamber. These valving components will continue to be held together after the pump chamber pressures drop, due to axial binding or bias on the cylinder housing 225 created by the bearings 38, 40 and 44, and by the friction discs 60.

With the valve disc 262 effectively keyed to the cylinder housing 225, cylinder housing rotation will automatically shift the valving 230 to its next operative position corresponding to the filling or pumping cycles, upon the powered rotation of the drive member 36 or 136 by the respective drive 28 including the gearmotor 52 and drive belt 58 or by the respective drive 128 including the motor 152 and worm 156.

It will be understood that appropriate standard servo related controls be provided to coordinate the operation of the gearmotor 52 and motor 152 to achieve the desired flow rates and pressures. Further, stepper gearmotors or stepper motors might be used as a most accurate and readily controlled servo related system needed herein for the accurate pumping operations. A single PC might control all pump operations.

Moreover, alternative means can be used for locating the proper operating positions of the valving 30, 230, such as by replacing the axial guides 48, 48 and cross pin 46 and rollers 50 arrangement and using instead a pin-groove cooperation acting directly between the rotating cylinder housing 25, 225 and frame structure 20, 120, 220. The friction between the piston seals and cylinder/screw will minimize and/or preclude relative rotation between the screw and cylinder during pump operation.

Further, while reference has been made only of a single frame structure (20, 120 and 220) it is apparent that many separate components can be used and assembled together, as illustrated or as might otherwise be modified, to make up the unitary frame structure of the operative pump and valve assembly.

The disclosed pump and valve assembly can provide syringe type liquid delivery, with steady accurately controlled flow, capable of being reproduced for comparable test runs and reliable test confirmations. It can have a single stroke pumping capacity of perhaps 5–10 ml, enough to deliver during a single stroke the solvent needed to complete most test runs using 1 mm ID or 2 mm ID columns, and it can thereafter be easily and rapidly refilled for the next test run. This satisfies the recent trend toward HPLC methods oriented toward efficient use of smallbore, microbore and short LC columns, that use less solvent and run faster.

The valving is positive (no check valves), being powered when needed by pump powering motor, and is built into the overall assembly (including the sample injector port and mixing tee 79), eliminating many independent parts needed in other HPLC systems. The mated valving seats is between stationary frame structure and the movable cylinder housing, are extended substantially normal to and substantially symmetrical of the cylinder housing axis, and port to the pump chamber. Further, the cylinder housing effectively is axially constrained between the frame structure, by the bearings 38 and 40, rotatable drive member 36, 136, and friction disc 44 at the open end, and by the valving seats at disc face 62F at the closed pump chamber end, so that pumped pressures in the pump chamber bias the valving seats together with seating pressures proportional to the pumped pressures. This provides that the valve can be operated essentially without leakage and yet can be shifted without excessive surface wear between operative positions with the pumped liquid pressures being less than maximum. The dual piston sealing arrangement and inside cylinder wall flushing should extend the expected service life of the unit, with minimal solvent leakage damaging of the linear pump drive mechanism and solvent film or crust buildup on the cylinder wall that might reduce the overall pump efficiency. This further allows the each piston-cylinder pump structure to be powered by a linear drive lead screw concentrically positioned in the pump cylinder and closely adjacent the defined pump cylinder, making for a compact assembly. The assembly further is unitary and lightweight, allowing for space efficiency and ease of movement and set-up, for easy field sales and shipments, and for possible use as an optional OEM part in other LC systems.

The pump and valve assembly can be comprised of conventional basic bearing, seal and drive components, and the special framing, piston-cylinder or valving structures can be easily fabricated, making its manufacture of low cost overall, for encouraging its purchase and use, even to the extend of multiple unit purchases for added HPLC versatility. With the combined and adjacent pump and valving, minimal dead space regions are created; as does the complete discharge achieved with the piston-cylinder type pump, making for small volume economical solvent flushing between tests of different solvents.

While specific embodiments have been illustrated and discussed, minor changes could be made in an overall assembly without departing from the spirit of the inventive teaching. Accordingly, the invention is to determined by the scope of the following claims.

What is claimed is:

1. A liquid chromatographic pump and valve assembly for directing sample and solvent liquids from containment in respective reservoirs to a column, comprising the combination of frame structure, a pump, valving, and means supporting the pump and valving from the frame structure;

said pump having a cylinder with one end closed, a piston in sealed relationship in the pump cylinder whereby a variable volume pump chamber is defined at said one cylinder end as said piston is axially moved in the pump cylinder, means including a drive member rotatably supported by the frame structure adjacent the other open end of the pump cylinder for shifting the piston axially therewithin responsive to rotation of the drive member and whereby drive member rotation in one direction effectively shifts the piston to increase the chamber volume and provide a filling cycle and whereby drive member rotation in the opposite direction effectively shifts the piston to decrease the chamber volume and provide a pumping cycle, and power means for rotating the drive member;

said valving being operable in a filling position to communicate the sample reservoir to the column and to communicate the solvent reservoir to the pump chamber and being operable in a pumping position to isolate both the sample and solvent reservoirs and to communicate the pump chamber to the column; and means coupling said drive member to the valving operable to shift said valving to said filling position and to said pumping position responsive to the initial rotation of said drive member at the beginning of each respective filling and pumping cycle.

2. The liquid chromatographic pump and valve assembly according to claim 1, further with said cylinder comprising a housing and means supporting the cylinder housing to rotate concentrically of its longitudinal axis relative to the frame structure, means limiting cylinder housing rotation to less than a full revolution relative to the frame structure, and said coupling means including having said cylinder housing linked mechanically to said valving, operable then upon the initial drive member rotation at the beginning of each respective filling and pumping cycle to rotate said cylinder housing and shift said valving to said respective filling and pumping positions.

3. The liquid chromatographic pump and valve assembly according to claim 2, further comprising the valving having a valve member and means coupling the valve member to the cylinder housing, said valve member having a face cooperating against a frame structure seat extended substantially normal to and substantially symmetrical of the cylinder housing axis, and said frame structure seat being ported to the liquid reservoirs and the column and said valve member having a through bore between the valve member face and the pump chamber, whereby pumped pressures in the pump chamber bias the valve member face against the frame structure seat to generate seating pressures therebetween proportional to the pumped pressures.

4. The liquid chromatographic pump and valve assembly according to claim 1, further comprising said piston having axially spaced sealing regions with the pump cylinder defining a chamber therebetween, one sealing region being immediately adjacent the pump chamber and the other sealing region being next to the one sealing region and remote from the pump chamber, and means including a port communicating the piston chamber to a location remote from the pump chamber, operable to have any liquid collected in the piston chamber drain to the vessel.

5. The liquid chromatographic pump and valve assembly according to claim 4, further comprising said one sealing region being axially fixed relative to the piston and the other sealing region being axially movable relative to the one sealing region to provide that said piston chamber defined therebetween has a variable volume during piston movement in the cylinder, a source of cleaning liquid located remote from the pumping chamber and means including said port communicating the piston chamber to said cleaning liquid operable to have the cleaning liquid drawn into the piston chamber during the pumping cycle when the piston chamber is increasing in volume effective to flush the pump cylinder wall and to have the cleaning liquid discharged from the piston chamber during the filling cycle when the piston chamber is decreasing in volume.

6. The liquid chromatographic pump and valve assembly according to claim 5, further comprising said means for shifting the piston including a screw, said piston regions being supported adjacent one end of the screw where the screw is extended axially of the cylinder in the direction away from the pump chamber, and said port and said means communicating the port to said cleaning liquid are formed in said screw.

7. The liquid chromatographic pump and valve assembly according to claim 6, further comprising said means communicating the port to said cleaning liquid including said screw having an axial bore.

8. The liquid chromatographic pump and valve assembly according to claim 7, further comprising a liner tube fitted in the bore and separating the screw from any liquid in the piston chamber, and the liner tube being of material suited to resist chemical attacks from any liquid in the piston chamber.

9. The liquid chromatographic pump and valve assembly according to claim 7, further with said cylinder comprising a housing and means supporting the cylinder housing to rotate concentrically of its longitudinal axis relative to the frame structure, means limiting cylinder housing rotation to less than a full revolution relative to the frame structure, and said coupling means including having said cylinder housing linked mechanically to said valving, operable upon initial drive member rotation at the beginning of each respective filling and pumping cycle to rotate said cylinder housing and shift said valving to said respective filling and pumping positions.

10. The liquid chromatographic pump and valve assembly according to claim 9, further comprising the valving having a valve member and means coupling the valve member to the cylinder housing, said valve member having a face cooperating against frame structure seat extended substantially normal to and substantially symmetrical of the cylinder housing axis, and said frame structure seat being ported to the liquid reservoirs and the column and said valve member having a through bore between the valve member face and the pump chamber, whereby pumped pressures in the pump chamber bias the valve member face against the frame structure seat to generate seating pressures therebetween proportional to the pumped pressures.

11. The liquid chromatographic pump and valve assembly according to claim 10, further comprising the means including a valve member and the closed end of the pump cylinder being immediately adjacent one another and adjacent the pump chamber.

12. The liquid chromatographic pump and valve assembly according to claim 10, further comprising a reversible electric motor having an output shaft extended transverse to the axis of rotation of the drive member, and a worm keyed to the motor shaft or coupled extension thereof operable to mesh with gearing on the perimeter of the drive member, operable to rotate said drive member and shift said piston.

13. A liquid chromatographic pump and valve assembly for directing sample and solvent liquids from containment in respective reservoirs to a column, comprising the combination of frame structure, a pump, valving, and means supporting the pump and valving from the frame structure;

said pump having a housing defining a cylinder with one end closed, a piston in sealed relationship in the pump cylinder whereby a variable volume pump chamber is defined at said one cylinder end as said piston is axially moved in the pump cylinder, a screw having a connection at one end to said piston and having the other end extended axially beyond the other open end of the cylinder, means including a rotatable drive member and a linear drive supported by the frame structure adjacent the other open end of the pump cylinder for shifting the piston axially within the cylinder responsive to rotation of the drive member and whereby drive member rotation in one direction effectively shifts the piston to increase the chamber volume and provide a filling cycle and whereby drive member rotation in the opposite direction effectively shifts the piston to decrease the chamber volume and provide a pumping cycle, means supporting the cylinder housing to rotate concentrically of its longitudinal axis relative to the frame structure, means limiting cylinder housing rotation to less than a full revolution relative to the frame structure, means coupling said drive member to said cylinder housing operable upon initial drive member rotation at the beginning of each respective filling and pumping cycle to rotate said cylinder housing, and power means for rotating the drive member; and means coupling said cylinder housing to the valving operable to shift said valving to a filling position and to a pumping position responsive to the initial rotation of said cylinder housing at the beginning of each respective filling and pumping cycle, and said valving being operable in a filling position to communicate the sample reservoir to the column and to communicate the solvent reservoir to the pump chamber and being operable in a pumping position to isolate both the sample and solvent reservoirs and to communicate the pump chamber to the column.

14. The liquid chromatographic pump and valve assembly according to claim 13, further comprising the valving having a valve member having a face cooperating against a frame structure seat extended substantially normal to and substantially symmetrical of the cylinder housing axis, said cylinder housing being shiftable axially slightly in the direction of the frame structure seat, and said frame structure seat being ported to the liquid reservoirs and the column and said valve member having a through bore between the valve member face and the pump chamber, whereby pumped pressures in the pump chamber bias the valve member face against the frame structure seat to generate seating pressures therebetween proportional to the pumped pressures.

15. The liquid chromatographic pump and valve assembly according to claim 14, further comprising a reversible electric motor having an output shaft extended transverse to the axis of rotation of the drive member, and a worm keyed to the motor shaft or coupled extension thereof operable to mesh with gearing on the perimeter of the drive member, operable to rotate said drive member and shift said piston.

16. The liquid chromatographic pump and valve assembly according to claim 14, further comprising said piston having axially spaced sealing regions with the pump cylinder defining a chamber therebetween, one sealing region being immediately adjacent the pump chamber and the other sealing region being next to the one sealing region and remote from the pump chamber, and means including a port communicating the piston chamber to a location remote from the pump chamber, operable to have any liquid collected in the piston chamber drain to the vessel.

17. The liquid chromatographic pump and valve assembly according to claim 16, further comprising said one sealing region being axially fixed relative to the piston and the other sealing region being axially movable relative to the one sealing region to provide that said piston chamber defined therebetween has a variable volume during piston movement in the cylinder, a source of cleaning liquid located remote from the pumping chamber and means including said port communicating the piston chamber to said cleaning liquid operable to have the cleaning liquid drawn into the piston chamber during the pumping cycle when the piston chamber is increasing in volume effective to flush the pump cylinder wall and to have the cleaning liquid discharged from the piston chamber during the filling cycle when the piston chamber is decreasing in volume.

* * * * *